US008763608B2

(12) United States Patent
Meliniotis et al.

(10) Patent No.: US 8,763,608 B2
(45) Date of Patent: Jul. 1, 2014

(54) INHALER

(75) Inventors: Andreas Mark Meliniotis, Cambridge (GB); Stephen William Eason, Cambridge (GB); Roger William Clarke, Cambridge (GB); Liam Philip McGuinness, Herts (GB)

(73) Assignee: Vectura Delivery Devices Limited, Chippenham (GB)

( * ) Notice: Subject to any disclaimer, the term of this patent is extended or adjusted under 35 U.S.C. 154(b) by 338 days.

(21) Appl. No.: 13/155,131

(22) Filed: Jun. 7, 2011

(65) Prior Publication Data

US 2012/0138055 A1      Jun. 7, 2012

(30) Foreign Application Priority Data

Nov. 26, 2010   (GB) .................................. 1020130.9

(51) Int. Cl.
*A61M 15/00* (2006.01)
*A61M 16/00* (2006.01)
(52) U.S. Cl.
USPC .................................................. 128/203.21
(58) Field of Classification Search
USPC .............. 128/200.14, 203.15, 203.19, 203.21
See application file for complete search history.

(56) References Cited

U.S. PATENT DOCUMENTS

| 2009/0007908 A1* | 1/2009 | Eason et al. ............. 128/203.15 |
| 2010/0242960 A1 | 9/2010 | Zangerle |
| 2010/0258118 A1 | 10/2010 | Morton |
| 2010/0288278 A1 | 11/2010 | Pocock et al. |

FOREIGN PATENT DOCUMENTS

| EP | 2082770 A1 | 7/2009 |
| EP | 2082771 | 7/2009 |
| EP | 2082772 A1 | 7/2009 |
| GB | 2407042 | 4/2005 |
| WO | WO 03013633 | 2/2003 |
| WO | WO2005/037353 A1 | 4/2005 |
| WO | WO 2007/012871 | 1/2007 |
| WO | WO2009/007352 A2 | 1/2009 |
| WO | WO2009/092652 A1 | 7/2009 |
| WO | WO 2009092770 | 7/2009 |
| WO | WO 2011/049541 | 4/2011 |

OTHER PUBLICATIONS

Search Report from the Intellectual Property Office of the United Kingdom, dated Sep. 12, 2012, issued in connection with corresponding British Application No. GB1209263.1.

(Continued)

*Primary Examiner* — Kristen Matter
(74) *Attorney, Agent, or Firm* — Davidson, Davidson & Kappel, LLC

(57) ABSTRACT

An inhaler comprising a housing to receive a strip having a plurality of blisters is disclosed. Each blister has a puncturable lid and contains a dose of medicament for inhalation by a user. A mouthpiece is pivotally mounted to the housing through which a dose of medicament is inhaled by a user. The inhaler also has an actuating mechanism including a lever operable to sequentially move each blister into alignment with a blister piercing member depending from the mouthpiece. The actuating lever is also operable to cause the mouthpiece to pivot so that the blister piercing member punctures the lid of an aligned blister so that, when a user inhales through the mouthpiece, an airflow through the blister is generated to entrain the dose contained therein and carry it, via the mouthpiece, into the user's airway.

24 Claims, 13 Drawing Sheets

(56) References Cited

OTHER PUBLICATIONS

International Search Report from the International Searching Authority, mailed on May 24, 2012, issued in connection with corresponding International Application No. PCT/GB2011/052338.

Search report issued in GB1109493.5 dated Sep. 29, 2011.
Search Report from the Intellectual Property Office of the United Kingdom, dated Dec. 13, 2011, issued in connection with corresponding British Application No. GB1115000.0.

* cited by examiner

INHALER

FIELD OF THE INVENTION

This application claims priority to Great Britain Application No. 1020130.9 filed Nov. 26, 2010 the disclosure of which is hereby incorporated by reference,

BACKGOUND

The present invention relates to an inhalation device for oral or nasal delivery of medicament in powdered form. More specifically, the invention relates to an inhaler having a housing to receive a strip having a plurality of blisters spaced along the length of the strip, each blister having a puncturable lid and containing a dose of medicament for inhalation by a user. The invention also relates to an inhaler containing a strip of blisters each having a puncturable lid and containing a dose of medicament for inhalation by a user of the device according to the invention.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable lid which is permanently heat-sealed around the periphery of the blister during manufacture and after the dose has been introduced into the blister. A foil blister is preferred over capsules as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a number of blisters each containing an individual dose of medicament. When a dose is to be inhaled, an indexing mechanism moves a previously emptied blister away from the opening mechanism so that a fresh one is moved into a position ready to be opened for inhalation of its contents.

An inhaler of the type described above is known from the Applicant's own co-pending international application that has been published as WO2005/037353 A1.

According to one embodiment described and claimed in WO 2005/037353 A1, and illustrated in FIGS. 1 and 2 of the accompanying drawings, an inhaler 1 has a housing 2 containing a coiled strip of blisters 3. An indexing mechanism 4 comprising a single actuating lever 5 unwinds the coil 3 one blister at a time so that they pass over a blister locator chassis 6 and successively through a blister piercing station 7, when the actuator 5 is pivoted in a direction indicated by arrow "A" in FIG. 2. The blister 3a located at the blister piercing station 7 on each movement of the actuator 5 is pierced on the return stroke of the actuator 5 (in the direction indicated by arrow "B" in FIG. 2) by piercing elements 8 on the actuator 5 itself so that, when a user inhales through a mouthpiece 9, an airflow is generated within the blister 3a to entrain the dose contained therein and carry it out of the blister 3a via the mouthpiece 9 and into the user's airway.

The device known from WO2005/037353 A1 has already been modified so as provide a fully integrated device, i.e. one in which the used blisters are retained within its housing so that a user never has to come into direct contact with the blister strip. In one modified embodiment, known from the Applicant's own previous application that has now been published as WO09/007,352 A1, there is provided a flexible and resilient spiral element mounted within the housing of the device into which the used portion of the blister strip is directed so that, as the strip is gradually used up, the spiral expands as more and more of the strip is fed or pushed into it between its coils. The inhaler of the present invention, in its preferred form, is also a fully integrated device that retains the used blisters, although in a preferred embodiment it has a wall to separate the interior of the housing into used and unused blister compartments. The wall is preferably rigid and slideably mounted so that the size of the unused and used blister compartments changes relative to each other as the number of blisters that are used increases and the number of unused blisters decreases.

The aforementioned document also describes an embodiment in which used blisters are crushed between the blister strip drive or indexing wheel and the inner surface of the casing of the device, which is also a feature of the inhaler of the present invention. As crushing takes place as the used strip passes around the blister strip drive member, a curl or curved form is imparted to the strip which helps it to coil up within the chamber.

The inhaler of the invention may also incorporate a blister strip drive mechanism or indexing mechanism that forms the subject of the Applicant's own previous international application that has now published as WO2009/092652 A1.

The disclosures of WO2005/037353 A1, WO09/007,352 A1 and WO2009/092652 A1 are all incorporated herein by reference.

SUMMARY OF THE INVENTION

The present invention seeks to provide another inhalation device of the type disclosed in the above-mentioned applications, and which also has a relatively simple construction, is robust, straightforward to manufacture and easy for the patient to use.

According to the invention, there is provided an inhaler comprising a housing to receive a strip having a plurality of blisters, each blister having a puncturable lid and containing a dose of medicament for inhalation by a user, a mouthpiece mounted to the housing and through which a dose of medicament is inhaled by a user, a blister piercing member mounted for rotation about a first axis and an actuating mechanism including an actuating lever mounted for rotation about a second axis to sequentially move each blister into alignment with the blister piercing member, wherein the actuating lever cooperates with the blister piercing member so that the blister piercing member pivots about said first axis in response to rotation of the actuating member from an initial position about the second axis to puncture the lid of an aligned blister so an airflow through the blister is generated to entrain the dose contained therein and carry it, via the mouthpiece, into the user's airway when a user inhales through the mouthpiece.

In a preferred embodiment, the blister piercing member is fixed to the mouthpiece and the mouthpiece is pivotally mounted to the housing so that the mouthpiece pivots, together with the blister piercing member, about said first axis in response to rotation of the actuating lever about the second axis.

In another embodiment, the blister piercing member is pivotally mounted to the mouthpiece for rotation about said first axis so that the blister piercing member pivots about said first axis relative to the mouthpiece, in response to operation of the actuating lever.

Preferably, the actuating lever is pivotable in the same direction about the second axis to sequentially move each blister into alignment with a blister piercing member and to cause rotation of the blister piercing member about the first axis so that the blister piercing member punctures the lid of an aligned blister.

The actuating mechanism may be configured such that rotation of the actuating lever about the second axis through a first portion of its stroke moves a blister into alignment with a blister piercing member and, further rotation of the actuating lever about the second axis in the same direction, during a second portion of its stroke, causes rotation of the blister piercing member about the first axis so that the blister piercing member punctures the lid of an aligned blister.

The actuating mechanism may include a blister strip drive wheel and the actuating lever may be engaged with said blister strip drive wheel during rotation of the actuating lever to rotate said blister strip drive wheel and drive said strip.

In a preferred embodiment, the actuating mechanism is configured such that the actuating lever and blister strip drive wheel disengage at the end of the first portion of the stroke so that the blister strip drive wheel remains substantially stationary during rotation of the actuating lever through said second portion of its stroke.

Preferably, the actuating mechanism comprises a drive coupling member rotatable in response to rotation of the actuating lever to rotate the blister strip drive wheel, the blister strip drive wheel being rotatably mounted on said drive coupling member, wherein the actuating mechanism includes means to control rotation of the blister strip drive wheel relative to rotation of the drive coupling member so that the blister strip drive wheel rotates together with the drive coupling member during the first portion of the stroke of the actuating lever but not during the second portion of the stroke of the actuating lever.

In a preferred embodiment, the means for controlling rotation of the blister strip drive wheel is also configured to inhibit rotation of the blister strip drive wheel when the actuating lever is rotated in the opposite direction.

The drive coupling member may include a drive gear rotatable together with the drive coupling member and the actuating lever can include a drive gear segment that drivingly engages with the drive gear member so that the drive gear rotates in response to rotation of the actuating lever to rotate the drive coupling to member.

Preferably, the means to control rotation of the blister strip drive wheel includes cooperating elements on the drive coupling member and on the housing.

In an embodiment where the mouthpiece is pivotally mounted together with the blister piercing element, one of the actuating lever and the mouthpiece can have a drive cam element and the other of the actuating lever and the mouthpiece can have a drive cam surface. The drive cam element cooperates with the drive cam surface so that the mouthpiece pivots about said first axis in response to rotation of the actuating member about the second axis to puncture the lid of an aligned blister.

The cam groove may have an arcuately shaped region having an axis that corresponds to the second axis about which the actuating lever rotates such that, during said initial rotation of the actuating lever through its first portion of its stroke, the drive cam element slides along said arcuately shaped region of the cam groove without causing rotation of the mouthpiece about the first axis.

In this embodiment, the cam groove can have a second region shaped such that, during further rotation of the actuating lever through its second portion of its stroke, cooperation between the drive cam element and the second region of the cam groove causes the mouthpiece to rotate at the same time as the actuating lever so that the blister piercing element punctures the lid of an aligned blister.

Alternatively, in the embodiment where the blister piercing element is pivotally mounted to a fixed housing, one of the actuating lever and the blister piercing member can have a drive cam element and the other of the actuating lever and the blister piercing member can have a drive cam surface. The drive cam element cooperates with the drive cam surface so that the blister piercing element pivots about said first axis in response to rotation of the actuating member about the second axis to puncture the lid of an aligned blister.

The cam groove can have an arcuately shaped region having an axis that corresponds to the second axis about which the actuating lever rotates such that, during said initial rotation of the actuating lever through its first portion of its stroke, the drive cam element slides along said arcuately shaped region of the cam groove without causing rotation of the blister piercing member about the first axis.

The cam groove may have a second region shaped such that, during further rotation of the actuating lever through its second portion of its stroke, cooperation between the drive cam element and the second region of the cam groove causes the blister piercing element to rotate together with the actuating so that the blister piercing element punctures the lid of an aligned blister.

In any of the embodiments, the inhaler may comprise a cap and a coupling pivotally mounting the cap to the housing for rotation about a third axis, the cap covering the mouthpiece in a closed position.

The housing preferably comprises a shell and the actuating lever is mounted for rotation about the second axis on the shell and includes a mounting plate that extends within a space between the shell and the cap.

In one embodiment, the actuating lever comprises a button extending from said plate and protruding out of said space to enable actuation of the actuating lever by a user.

Preferably, the actuating lever comprises an arcuately shaped opening extending about the second axis, the coupling that pivotally mounts the cap to the housing extending through said opening so that the coupling travels along the arcuately shaped opening as the actuating lever pivots about the second axis.

The cap and actuating lever may include cooperating means configured such that, when the cap is rotated from its open position back into its closed position in which it covers the mouthpiece, the actuating lever is rotated rotate back into its initial position.

Preferably, the cooperating means comprises a wall on the actuating lever and a drive member depending from the cap towards the actuating lever, said wall and drive member being positioned between the second and third axes such that the drive member engages the wall when the cap is rotated in a direction back into its closed position to rotate the actuating member about the second axis back into its initial position.

In any embodiment, the inhaler may include a detent mechanism such as a cantilevered arm on the actuating lever and a pawl on the shell, the arm being resiliently deformed by said pawl as the actuating lever reaches the end of the second portion of its stroke, to hold the actuating lever in position until the cap is closed.

The cantilevered arm preferably includes a kinked portion that snaps over the pawl when the actuating lever is rotated towards the end portion of its stroke.

In a preferred embodiment, a wall is slideably mounted in the housing to divide it into unused and used blister compartments.

The wall preferably comprises a baffle extending between opposing housing walls and an elongate foot extending substantially at right-angles to the baffle and being slideably received within a recess in a surface of a wall of the housing.

The baffle is preferably attached to a central region of the foot.

In a preferred embodiment, the foot is widest at its ends remote from the baffle such that only the ends of said foot contact the walls of said recess in the housing.

According to another aspect of the invention, there is provided an inhaler comprising a housing to receive a strip having a plurality of blisters, each blister having a puncturable lid and containing a dose of medicament for inhalation by a user, a mouthpiece pivotally mounted to the housing and through which a dose of medicament is inhaled by a user and an actuating mechanism including a lever operable to sequentially move each blister into alignment with a blister piercing member depending from the mouthpiece said actuating lever also being operable to cause the mouthpiece to pivot so that the blister piercing member punctures the lid of an aligned blister so that, when a user inhales through the mouthpiece, an airflow through the blister is generated to entrain the dose contained therein and carry it, via the mouthpiece, into the user's airway.

A cap is preferably pivotally mounted to the housing that covers the mouthpiece in a closed position.

The cap may extend over the actuating lever in a closed position.

In one embodiment, the actuating lever is pivotally mounted to the housing and the actuating mechanism is configured such that the actuating lever is pivotable to sequentially move each blister into alignment with a blister piercing member and also pivotable to cause rotation of the mouthpiece so that the blister piercing member punctures the lid of an aligned blister.

The actuating lever is preferably pivotable in the same direction to sequentially move each blister into alignment with a blister piercing member and to cause rotation of the mouthpiece so that the blister piercing member punctures the lid of an aligned blister.

The actuating mechanism may be configured such that an initial rotation of the actuating lever through a first portion of its stroke moves a blister into alignment with a blister piercing member and, further rotation of the actuating lever causes rotation of the mouthpiece so that the blister piercing member punctures the lid of an aligned blister.

In a preferred embodiment, the actuating mechanism is configured such that movement of the strip stops between said initial and further rotation of the actuating lever.

The actuating mechanism preferably includes a blister strip drive wheel around which a blister strip received in the housing is fed, said blister strip drive wheel being rotatable in response to rotation of the actuating lever to drive said strip.

In one embodiment, wherein the blister strip drive member comprises a plurality of spokes extending from a hub, the spokes being spaced from each other such that a spoke locates between blister cavities as a blister strip passes around the blister strip drive member to engage and drive a strip as the blister strip drive member rotates, the blister strip drive member being positioned relative to a wall such that the distance between the hub and said wall is less than the height of a blister cavity such that onward rotation of the wheel causes a blister cavity to be at least partially squashed or sandwiched between the hub and said wall.

The inhaler preferably includes a drive coupling member rotatable in response to rotation of the actuating lever, the blister strip drive wheel being rotatably mounted on said drive coupling member, the drive coupling member and the housing including means to control rotation of the blister strip drive member relative to rotation of the drive coupling member so that the blister strip drive wheel rotates together with the drive coupling member during part of the rotation of the drive coupling member in the same direction.

In one embodiment, the means for controlling rotation is configured so that the blister strip drive wheel rotates together with the drive coupling member during part of the rotation of the drive coupling member in the same direction and the blister strip drive wheel does not rotate at all when the drive coupling member rotates in the opposite direction.

The drive coupling member may include a drive gear member and the actuating lever includes a drive gear segment that drivingly engages with the drive gear member so that the drive gear member rotates in response to rotation of the actuating lever. The drive coupling member and the drive gear member may be integrally formed as one component.

Preferably, the actuating lever includes a mouthpiece drive cam element that cooperates with a cam groove formed in the mouthpiece.

The cam groove in the mouthpiece can have an arcuately shaped region such that, during said initial rotation of the actuating lever through its first portion of its stroke, the drive cam element slides along the cam groove with substantially no rotation of the mouthpiece.

The cam groove may also have a second region shaped such that, during further rotation of the actuating lever beyond the first portion of its stroke, cooperation between the drive cam element and the cam groove causes the mouthpiece to rotate together with the actuating lever to pull the blister piercing element depending therefrom into the lid of an aligned blister.

The cap and the actuating lever may be configured such that, when the cap is rotated from an open position back into its closed position, the cap cooperates with the actuating lever to cause it to rotate back into its initial position.

Rotation of the actuating lever back into its initial position in response to rotation of the cap may also cause the drive cam element to slide back along the cam groove and lift the mouthpiece back into its original position in which the blister piercing element is removed from the aligned blister.

In a preferred embodiment, the cap includes a drive pin that cooperates with the actuating lever during closure of the cap so that the actuating lever is also rotated back to its initial position.

The actuating lever may have a hole therethrough and the drive pin extends from the cap into said hole, the drive pin engaging with the sidewall of said hole when the cap is rotated from its open into its closed position.

In one embodiment, the housing comprises a shell that defines a chamber to receive a blister strip, the blister strip drive wheel being received in the shell, the shell having opposing end walls spaced from each other by a side wall, the drive coupling member extending through a hole in one of said opposing end walls such that the drive gear is disposed on the outside of the shell.

The actuating member may comprise a plate extending between an actuating button and the gear segment, said plate extending across a surface of an end wall on the outside of the shell.

The actuator can be pivotally mounted to a hub upstanding from said surface.

The actuating member may also comprise a second plate that extends parallel and spaced from the first plate, the shell being received between said plates and said second plate being pivotally mounted to a hub upstanding from the surface of said opposite end wall of the shell.

In one embodiment, the mouthpiece has a peripheral wall that extends across the surface of the outside of the shell.

The actuating lever may include an actuating button that extends between said plates and across the side wall of the shell.

The cap can have parallel side wall sections spaced from each other by an intermediate section, the side wall sections each extending across a corresponding end wall of the shell, one of said side wall sections of the cover enclosing the first and second plates of the actuating lever and at least a portion of the side wall of the mouthpiece.

The intermediate section may extend across the side wall of the shell and covers the mouthpiece in a closed position.

In one embodiment, a boss upstands from opposite surfaces of the shell each of which locate in a recess in a corresponding side wall section of the cap to pivotally mount the cap to the shell.

BRIEF DESCRIPTION OF THE DRAWINGS

Embodiments of the invention will now be described, by way of example only, with reference to FIGS. 3 to 16 of the accompanying drawings, in which.

DETAILED DESCRIPTION

Figure 3:
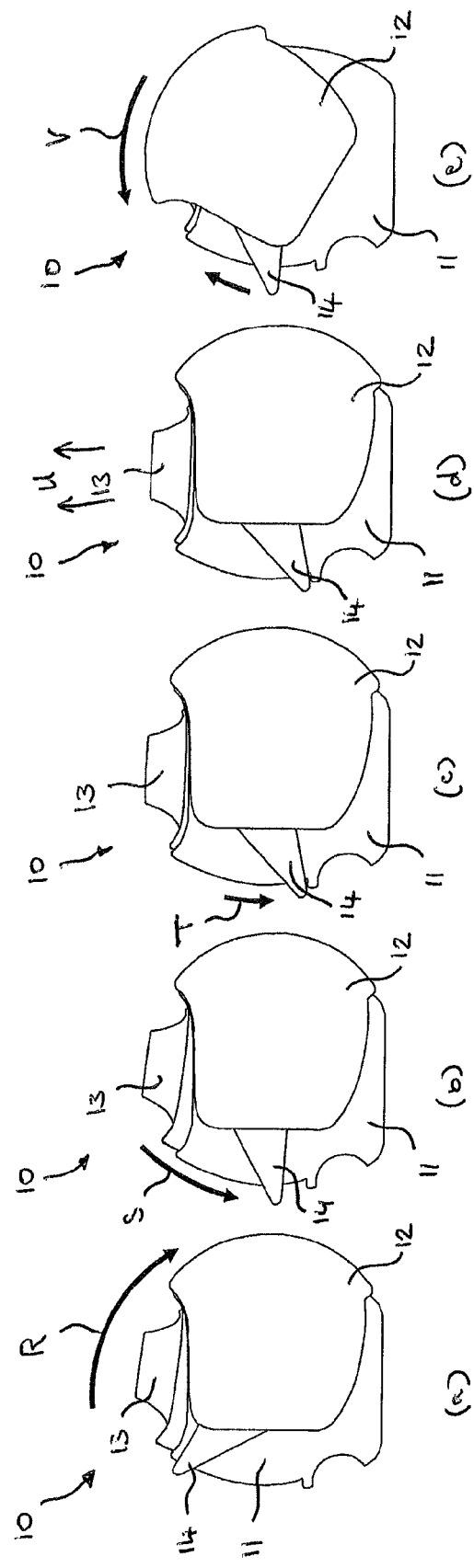
FIGS. 3a to 3e is a sequence of drawings to show the general function and operation of the inhaler according to the invention.
Figure 4:
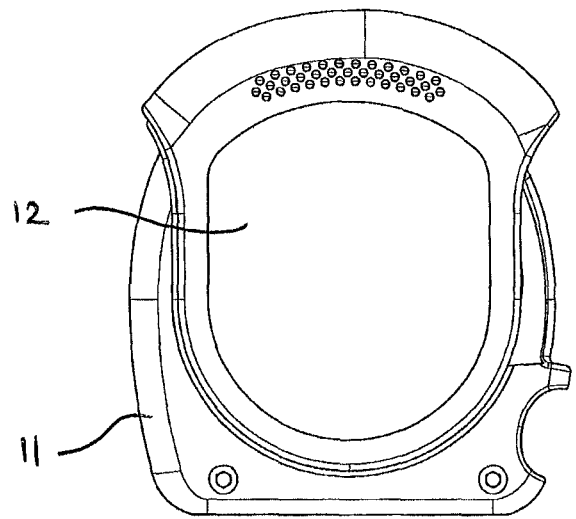
FIG. 4 is a side elevation of an inhalation device according to an embodiment of the invention.
Figure 5:
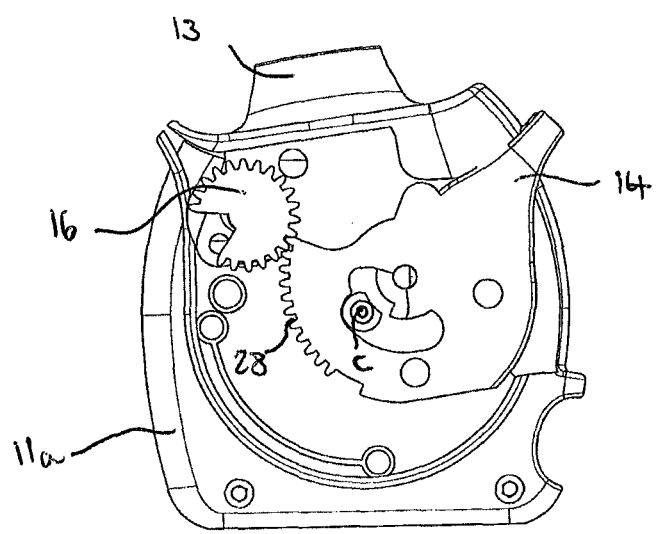
FIG. 5 is the side elevation of FIG. 4, but with the cap removed so that the internal components can be seen.
Figure 6:
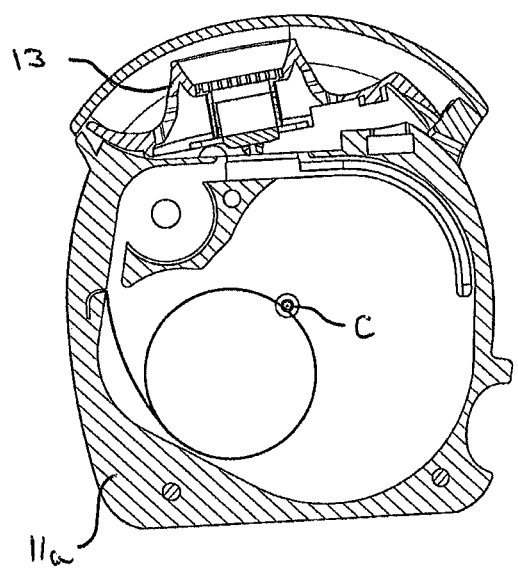
FIG. 6 is the side elevation of FIG. 5 after removal of one-half of the shell forming the housing of the inhaler.

Referring now to FIGS. 3a to 3e of the accompanying drawings, there is shown an inhaler 10 having a housing 11 formed from two shell portions 11a, 11b (see FIGS. 6 and 7), a cap 12 pivotally mounted to the housing 11 for rotation about an axis marked "C" (see FIGS. 5 to 7) from a closed position as shown in FIG. 4 in which the cap 12 covers and protects a mouthpiece 13 to a fully open position, as shown in FIGS. 3(b) to 3(d) and in a direction indicated by arrow "R" in FIG. 3(a), in which the mouthpiece 13 is exposed to enable a user to inhale a dose of medicament through the mouthpiece 13.

It should be noted that the cap is 'passive' in the sense that it can be opened and closed freely without performing the function of indexing of the blister strip or causing a blister piercing member 15 depending from the mouthpiece 13 to pierce the lid of an aligned blister.

The cap 12 is rotated into its fully open position in the direction of arrow "R". An actuating lever 14 is revealed as soon as the cap 12 is rotated out of its closed position. The user then applies pressure to the actuating lever 14, so that it rotates in the direction indicated by arrow "S" in FIG. 3(b).

During initial rotation of the actuating lever 14 through a first portion of its stroke into the position as it is shown in FIG. 3(b), the strip is indexed so as to move an unused blister into alignment with the blister piercing member 15.

When the actuating member is rotated through a second portion of its stroke beyond the position shown in FIG. 3(b) and after having completed the first portion of its stroke, in the direction of arrow "T" in FIG. 3(c), the strip remains stationary but the mouthpiece 13 is now pivoted so that the blister piercing member 15 pierces the lid of the previously aligned blister.

Although reference is made to a blister piercing member 15, it will be appreciated that multiple openings are formed in the lid of the blister so that air can be drawn into the blister through one or some of those openings and flow out of the blister together with an entrained dose of medicament, through one or more other openings and via the mouthpiece into a patient's airway.

Once the actuating lever is in the position shown in FIG. 3(c), the user now inhales through the mouthpiece 13, as shown by arrows indicated by "U" in FIG. 3(d).

After inhalation, the user rotates the cap in the opposite direction, i.e. in the direction indicated by "V" in FIG. 3(e). During this movement, the cap 12 engages with the actuating lever 14 so that the actuating lever 14 also returns to its initial position as shown in FIG. 3(a), the strip remaining stationary during this return movement of the actuating lever 14.

As mentioned above, the cap 12 is passive, although it does perform the function of re-setting the actuating member back to its original position in the event that the actuating lever is depressed prior to closing the cap.

As previously mentioned, the inhaler of the invention has an indexing mechanism that has previously been described with reference to WO2009/092652 A1. This aspect of the inhaler of the invention will now be described in detail with reference to FIGS. 8 to 13a. Although the drawings show a slightly different arrangement, in which an actuator 54 takes the place of a drive gear 16 attached to the drive coupling member 57 in the present invention, the principle remains the same as the actuator 54 and the drive gear are both rotated to index the strip. Therefore, rotation of the drive gear 16 performs the same function as rotation of the actuator 54 referred to in the description of FIGS. 8 to 13a below.

Figure 8:
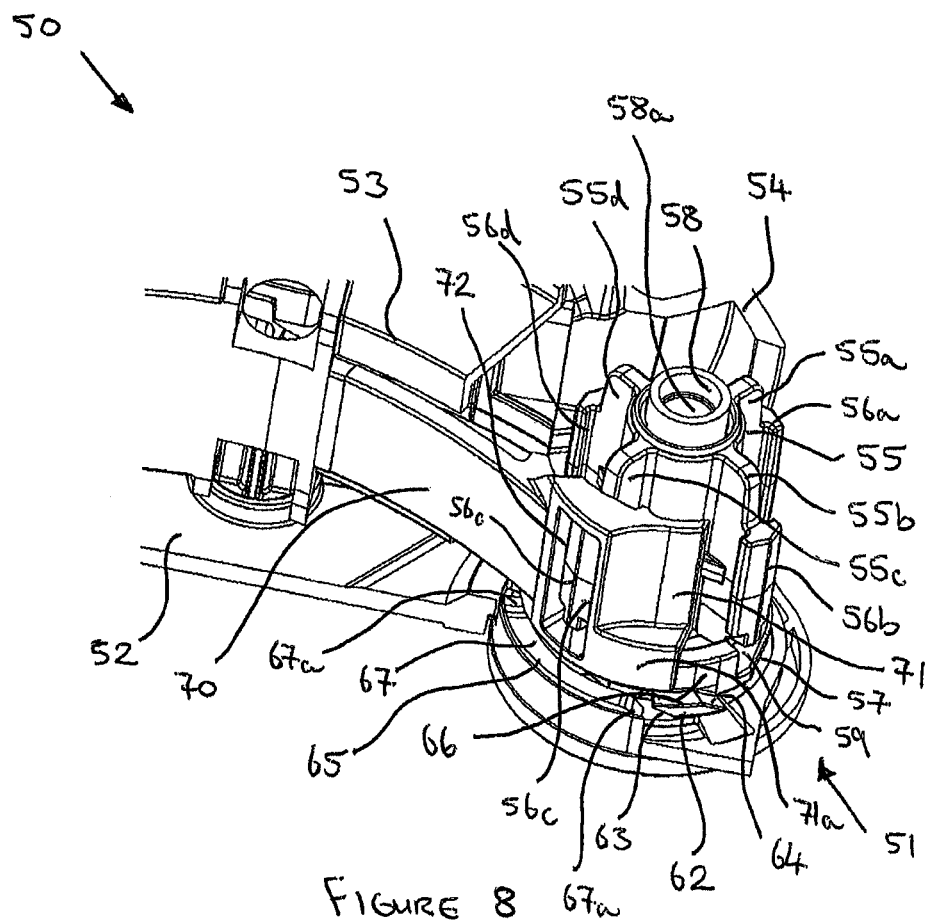
FIG. 8 is a partial perspective view of the blister strip indexing mechanism for use in the inhaler of the invention.
Figure 9:
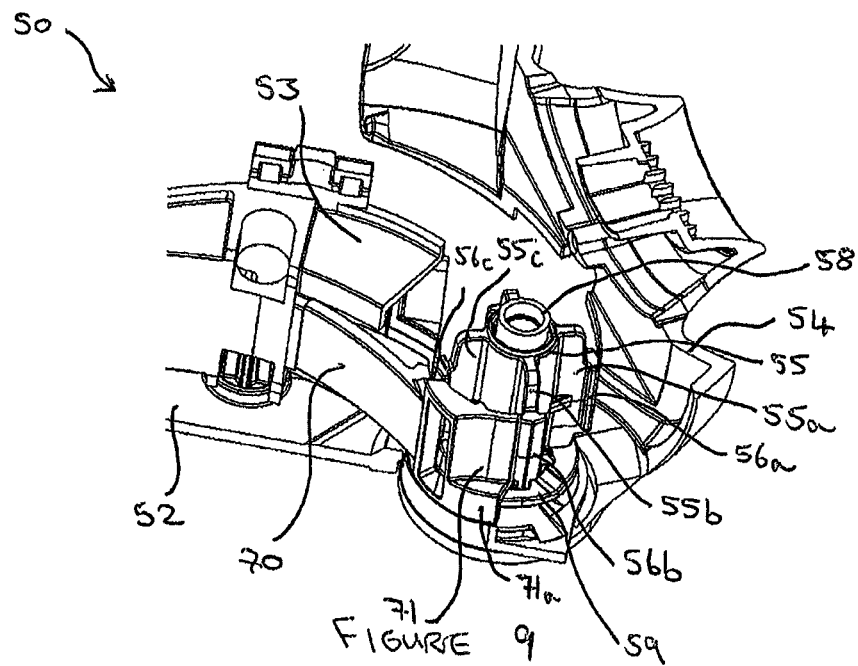
FIG. 9 is a partial perspective view of the blister strip indexing mechanism shown in FIG. 8 following partial rotation of the actuating lever into an intermediate position from its home position.
Figure 10:
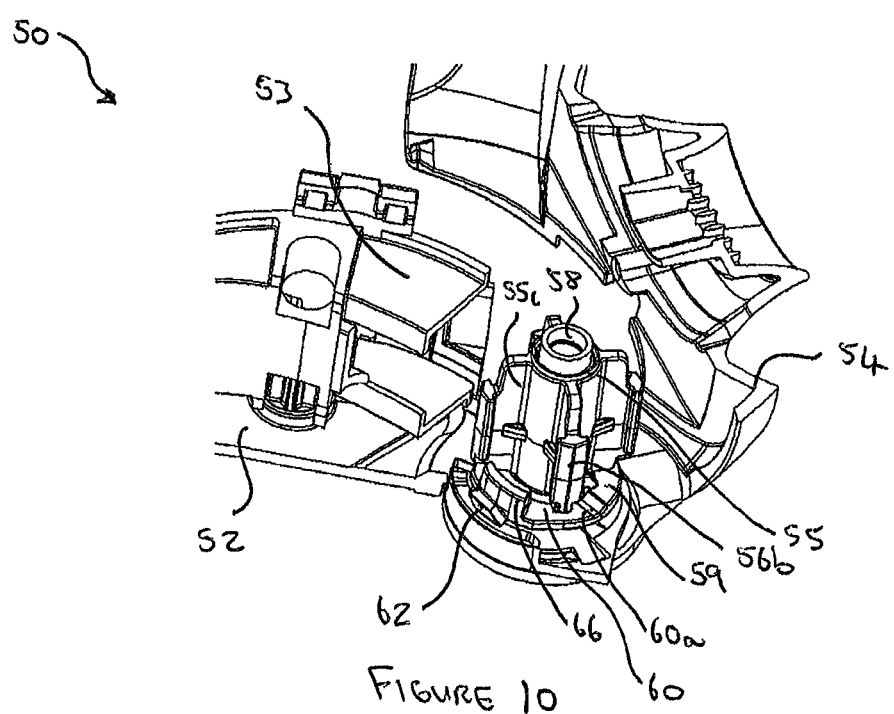
FIG. 10 is the same view as shown in FIG. 9, but without the optional cantilevered chassis arm.
Figure 11:
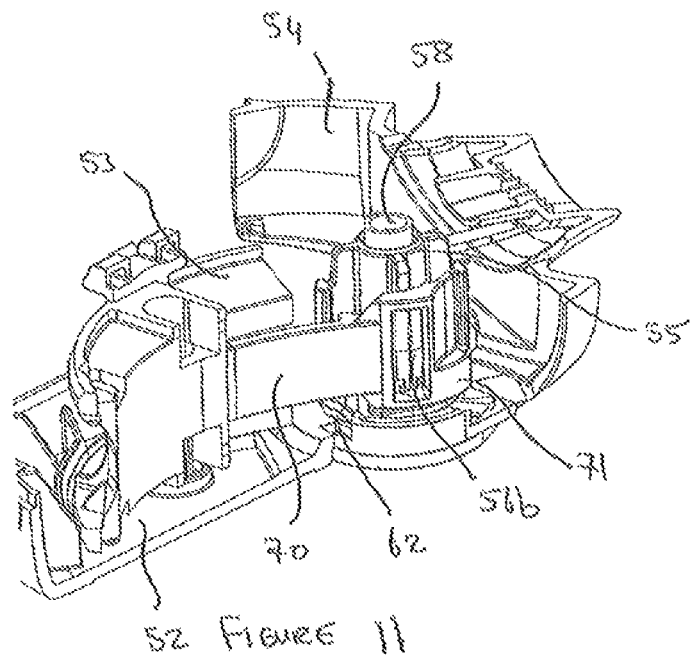
FIG. 11 is a partial perspective view of the blister strip indexing mechanism shown in FIGS. 8 to 10, after the actuating lever has been rotated to a point at which drive between the drive coupling and the actuator has disengaged.
Figure 12:
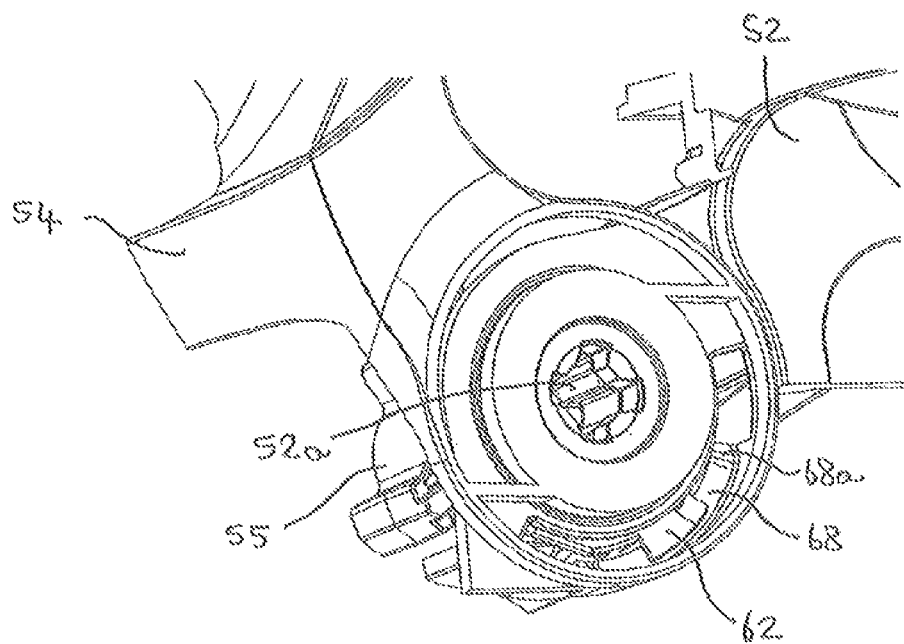
FIG. 12 is a partial perspective view of the opposite side of the indexing mechanism shown in FIGS. 9 to 11.
Figure 13A:
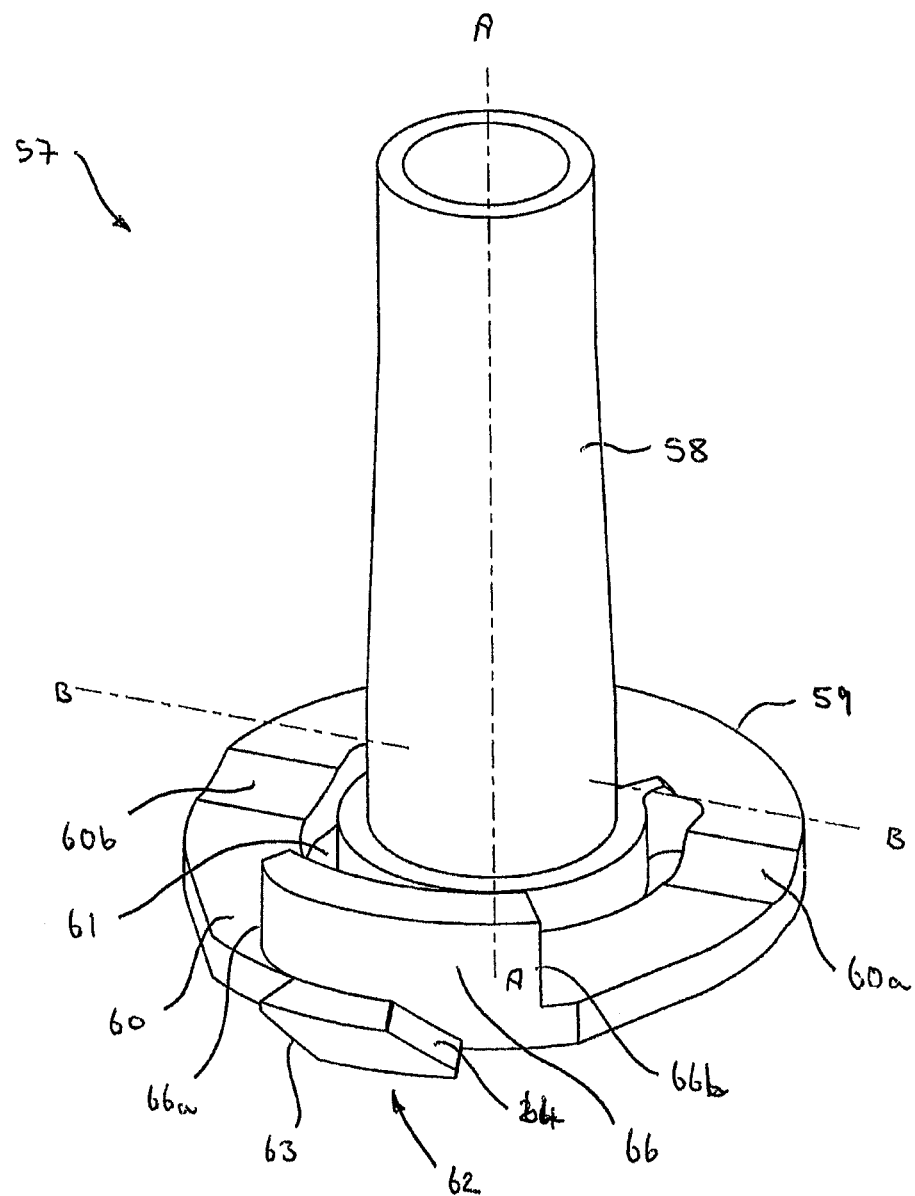
FIG. 13a is a perspective view of the drive coupling used in the indexing mechanism of the inhaler shown in FIGS. 9 to 12.
Figure 13B:
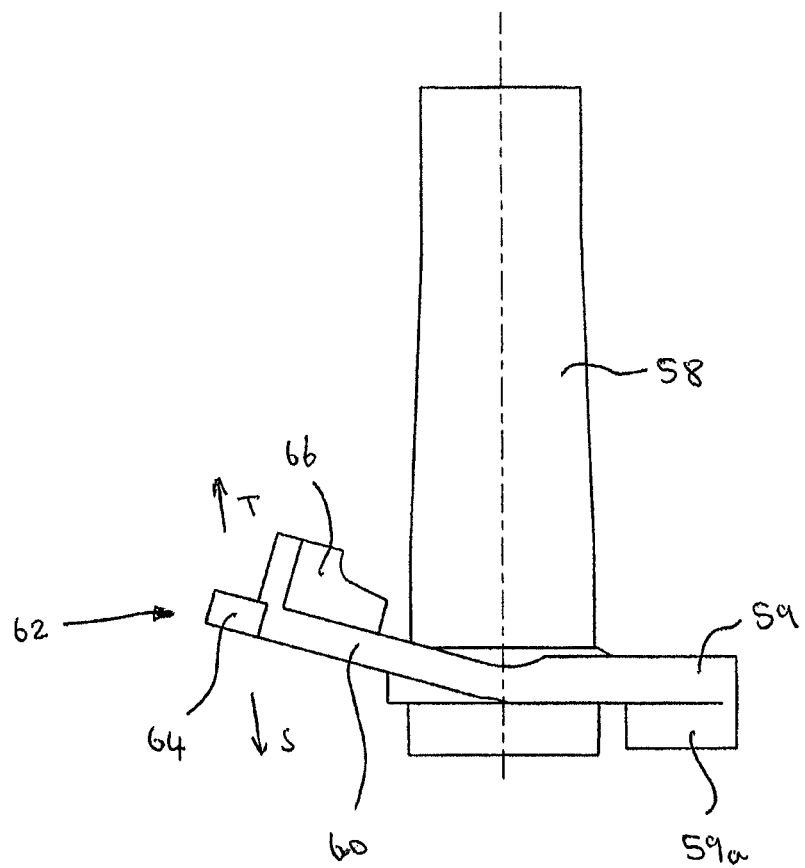
FIG. 13b is a side view of the drive coupling illustrated in FIG. 13a in which the flexible flange portion has been deflected in a direction "T" towards the shaft or, towards an indexing wheel mounted on that shaft.
Figure 14:
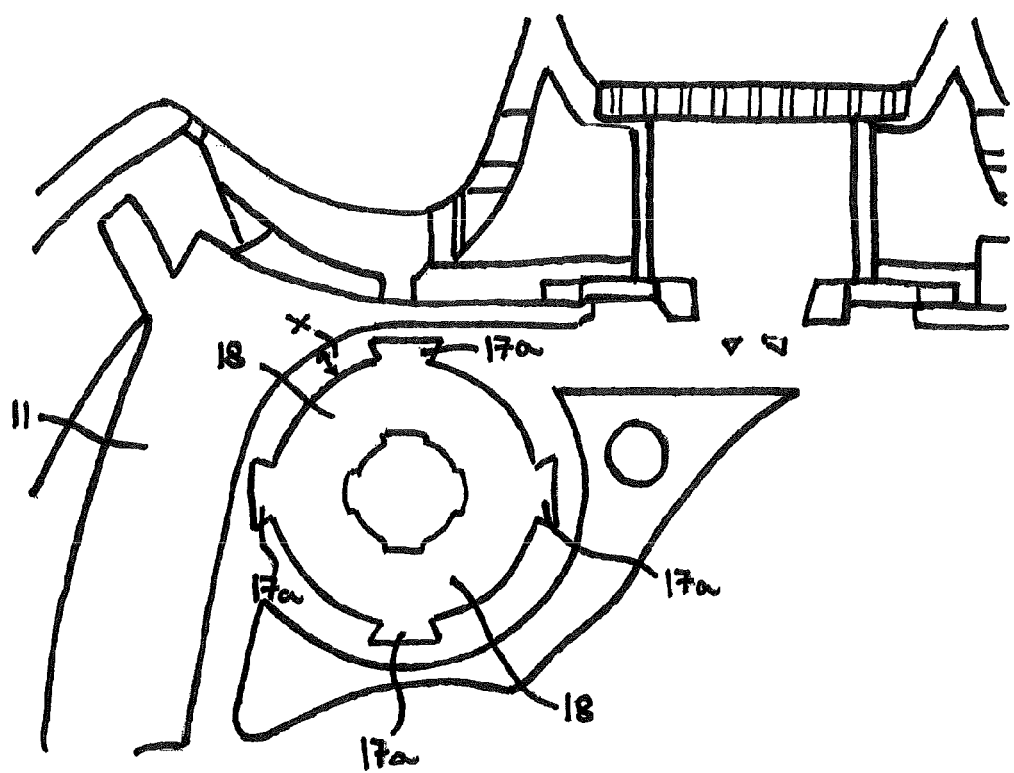
FIG. 14 is a partial view of the inhaler according to the invention showing the form and position of the indexing wheel that may be used in order to crush used blisters as they pass around the indexing wheel.

Referring now to FIG. 8, there is shown a partial perspective view of an inhalation device 50 comprising an indexing mechanism 51.

Figure 1:
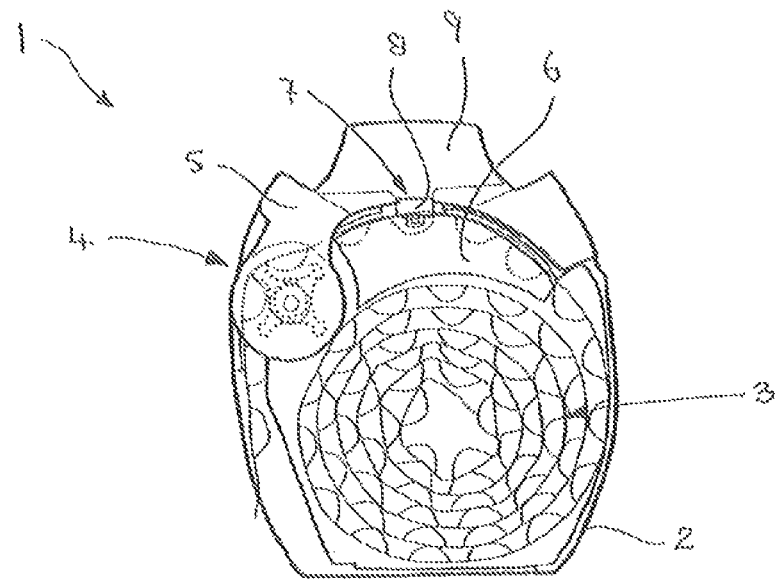
FIGS. 1 and 2 are side views of a conventional inhalation device to show how a strip is driven to sequentially move blisters into alignment with a blister piercing element by movement of an actuator from the position shown in FIG. 1 to the position shown in FIG. 2 which drives an indexing wheel. A piercing head on the actuator pierces the lid of an aligned blister when the actuator is returned to its normal position, as shown in FIG. 1.
Figure 2:
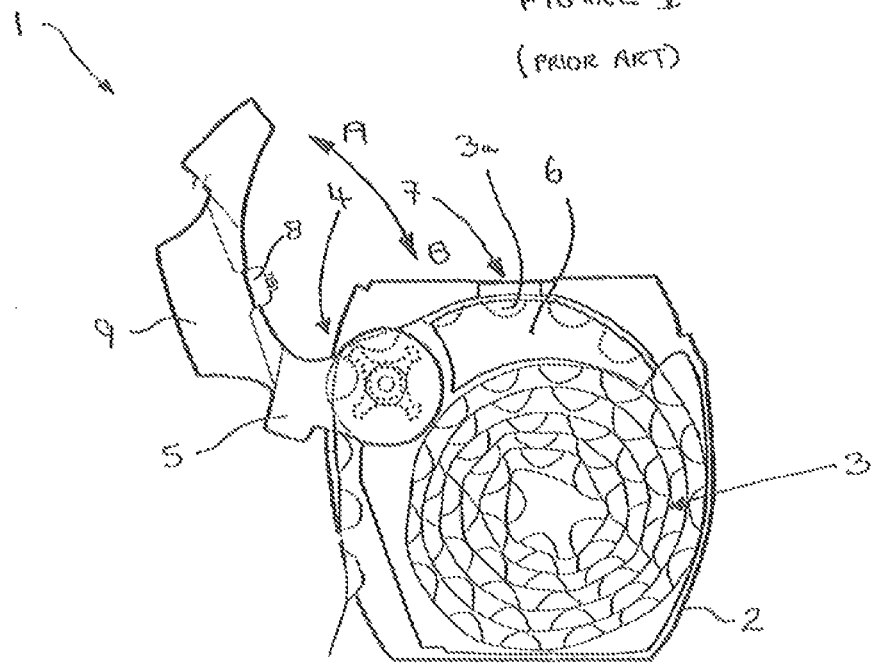

The indexing mechanism 51 includes an indexing wheel 55 comprising four vanes 55a,55b,55c,55d, each having an enlarged head portion 56a,56b,56c,56d. As is clear from reference to FIGS. 1 and 2, once a blister strip (not shown in FIGS. 8 to 14) has passed over the blister locating chassis 53, it passes around the indexing wheel 55. A blister locates in the space between two vanes 55a,55b,55c,55d so that, as the indexing wheel 55 rotates in response to rotation of the actuator 54, a vane 55a,55b,55c,55d engages a blister located between the vanes 55a,55b,55c,55d so as to drive the strip around the indexing wheel 55 to sequentially move each blister forward by a sufficient distance to move a fresh blister into alignment with a blister piercing element.

The indexing mechanism 51 includes a drive coupling member 57 (most clearly shown in FIGS. 13a and 13b) for selectively or temporarily coupling the actuator 54 to the indexing wheel 55 so that, when coupled, the indexing wheel 55 rotates in response to rotation of the actuator 54 to index the strip. The drive coupling member 57 comprises a shaft 58 defining an axis of rotation "A" (see FIGS. 13a and 13b) on which the indexing wheel 55 is rotatably received so that it can rotate freely about the shaft 58 about said axis of rotation "A". The actuator 54 is fixedly attached to the drive coupling member 57 (the gear drive would also be fixedly attached to the drive coupling member 57) so that the drive coupling member 57 rotates together with the actuator 54 at all times. In the embodiment illustrated and described with reference to FIGS. 8 to 12, the actuator 54, drive coupling member 57 and indexing wheel 55 are all mounted coaxially for rotation about the same axis "A". However, it will be appreciated that in the embodiment of FIG. 7, the mouthpiece 13 and actuating lever 14 are not coaxially mounted with Axis 'A'.

The drive coupling member 57 has a circular flange 59 that extends radially from one end of the shaft 58. A portion 60 of the flange is cut-away (see arcuate opening 61 in FIG. 8) over an angle of approximately 180 degrees where the flange 59 joins the shaft 58 so that this portion 60 of the flange 59 is not directly attached to the shaft 58 but only to the remaining portion of the flange 59 at each of its ends 60a,60b. As a result, this portion 60 of the flange 59 is flexible relative to the rest of the flange 59 and can be deflected out of the plane of the flange 59 that extends at right angles to the axis of the shaft, in an axial direction (indicated by "T" and "S", in FIG. 13b) either towards or away from the shaft 58 or, more importantly, towards or away from the indexing wheel 55 which is mounted on the shaft 58, when force is applied to it. This flexible flange portion 60 hinges about an axis B which intersects the axis A of the shaft 58 and actuator 54 but extends at right angles to it. The drive coupling member 57, or at least the flange 59, is made from a resilient material so that when the deflected flexible flange portion 60 is released, it returns to its neutral, unstressed position, in which it lies coplanar with the remaining fixed portion of the flange 59.

The flexible flange portion 60 has an integrally formed flange deflecting dog 62 projecting radially from its circumferential edge. The flange deflecting dog 62 has first and second angled engaging faces 63,64 on opposite sides. When the drive coupling member 57 is rotated in response to rotation of the actuator 54 in one direction, one of the first or second angled engaging faces 53,54 cooperate with a fixed formation 65 on the housing 52 to cause the flexible flange portion 60 to deflect in a first direction. When the drive coupling member 57 is rotated in the opposite direction, the other angled engaging face cooperates with the formation 65 on the housing 52 to cause the flexible flange portion 60 to deflect in a second, opposite direction, as will be explained in more detail below.

The flexible flange portion 60 also has an arcuately shaped indexing wheel drive dog 66 that upstands in an axial direction from its surface towards the indexing wheel 55 in the same direction as the shaft 58 and extends partially around the circumference of the flexible flange portion 60. As will now be explained in more detail below, an end face 66a (see FIG. 13a) of the indexing wheel drive dog 66 engages a vane 55a,55b,55c,55d of the indexing wheel 55 when the flexible flange portion 60 has been deflected in a first direction, as indicated by arrow "T" in FIG. 13b (the flange portion 60 is shown in its deflected position in FIG. 13b), so that the indexing wheel 55 is driven together with the drive coupling member 57.

As mentioned above, the flange deflecting dog 62 engages a formation 65 on the housing 52 when the drive coupling member rotates in response to rotation of the actuator 54 so as to flex the deflectable portion 60 of the flange 59. This formation 65 comprises first and second arcuately shaped tracks or paths 67, 68 positioned one above the other or spaced from each other in the axial direction. The surface of the innermost track 67 is visible in FIG. 8. The lower or outermost track 68 is located beneath it and is visible in FIG. 12. The ends of the tracks 67a, 68a have angled faces for reasons that will become apparent.

When the actuator 54 (or the drive gear) is rotated in a first direction, the drive coupling member 57 rotates together with it and the first outwardly facing angled surface 63 on the flange deflecting dog 62 contacts the angled face 67a of the innermost track 67. Further rotation of the drive coupling member 57 causes the flange deflecting dog 62 to ride up onto the surface of the innermost track 67 thereby deflecting the flexible flange portion 60 inwardly, i.e. in a direction into the housing 62 or towards the shaft 58 and the indexing wheel 55.

When the flexible flange portion 60 has been deflected inwardly in the direction of arrow T, further rotation of the drive coupling member 57 causes the indexing wheel drive dog 66 to engage a vane, which as shown in FIG. 8 is vane 55c, of the indexing wheel 55 so that the indexing wheel 55 rotates together with the drive coupling member 57 and drive to the indexing wheel 55 is engaged.

When the end of the innermost track 67 has been reached, the flange deflecting dog 62 falls off the surface of the track 67 and the resilience of the flexible flange portion 60 causes it to return to its original unstressed or neutral position. When the drive coupling member 57 is rotated further, the indexing wheel drive dog 66 no longer engages with the vane 55c of the indexing wheel 55 and instead passes beneath it so the indexing wheel 55 remains stationary. Therefore, drive to the indexing wheel 55 is disengaged, despite continued rotation of the actuator 54 in the same direction.

When the actuator 54 is rotated back in the opposite direction towards its home position, the second inwardly facing angled surface 64 of the flange deflecting dog 62 now contacts the lower or outermost track 68 so that the flange deflecting dog 62 now rides onto the surface of that second track 68, thereby causing the flexible flange portion 60 to deflect outwardly or in the opposite direction to the direction in which it was previously deflected. Engagement of the flange deflecting dog 62 with the outermost track 68 so as to deflect the flange portion 60 in the opposite direction, enables the drive coupling member 57 to rotate in the opposite direction without any drive to the indexing wheel 55. It will be appreciated that, if the flange portion 60 was not deflected in the opposite direction, the flange deflecting dog 62 would simply engage against the end of the formation 65 in the housing 62 when rotated back in the opposite direction, thereby preventing rotation in the opposite direction or, the flange deflecting dog 62 would travel back over the innermost track 67 deflecting the flexible flange portion 60 in the same direction causing the opposite end 66b of the indexing wheel drive dog 66 to engage with a vane 65b of the indexing wheel 65 thereby driving the indexing wheel 65 backwards rather than leaving it stationary with no drive engaged. Therefore, it is necessary to ensure that the flexible flange portion 60 is deflected in the opposite direction so that there is no drive to the indexing wheel during rotation of the coupling member 67 in the opposite direction.

When the drive deflecting dog 62 reaches the end of the outermost track 68, the flexible flange portion 60 returns to its original unstressed or neutral position, due to its resilience.

It will be appreciated that the extent of rotation of the indexing wheel 55 relative to the extent of rotation of the actuator 54 may be controlled by altering the circumferential length of the inner and outer tracks 67,68. If the tracks are made longer, the flexible flange portion 60 will be deflected for a greater proportion of the angle through which the actuator 54 is rotated and so the indexing wheel drive dog 66 will be engaged with the indexing wheel 55 to rotate the indexing wheel 55 throughout that angle. If required, the tracks 67,68 could be made sufficiently long so that the indexing wheel 55 rotates during rotation of the actuator 54 through its entire angle of movement in one direction. Alternatively, the tracks 67,68 could be made shorter to reduce the angle through which the actuator 54 and indexing wheel 55 rotate together.

Ideally, the track length can be selected so that the indexing wheel 55 is rotated through a sufficient angle to move the next, unused blister, into alignment with the blister piercing element.

The further rotation of the actuator 54 (the gear drive) causes the mouthpiece to rotate so that the blister piercing member pierces the lid of a blister that has just been moved into alignment with the blister piercing element.

It will be appreciated that the indexing mechanism 51 is designed to enable a stroke to be aborted when the actuator 54 or cap has been rotated through an angle which is sufficient to cause initial indexing of the strip but which is not such that the drive to the indexing wheel 55 has disengaged, i.e. a position in which the flange drive dog 62 has not reached the end of the innermost track 67. If the stroke is aborted and the actuator 54 returned to its original position before drive to the indexing wheel 55 has disengaged (or the drive gear rotated back to its initial position), the strip will be driven backwards into its original position as a rear surface 66b of the indexing wheel drive dog 66 will engage a preceding vane 55b to drive the indexing wheel 55 in the opposite direction.

The indexing mechanism 51 also includes optional means for locking the indexing wheel 55 to prevent its rotation between indexing steps and means for temporarily releasing that lock to allow rotation of the indexing wheel 55 when driven by the indexing wheel drive dog 66. The lock also improves positional accuracy of the strip and, more specifically, the next blister to be pierced. This locking arrangement will now be described in more detail below, although it should be noted that the locking mechanism can be omitted altogether.

The blister location chassis 53 may optionally comprise a resiliently flexible cantilever arm 70 that extends from the body 53 of the chassis towards the indexing wheel 55. The free end of the cantilever arm 70 has an enlarged head portion 71 comprising a letterbox shaped slot, window or opening 72 in which the head 56c of a vane 55c of the indexing wheel 55 is located. The opening 72 is dimensioned such that the head 56c of the vane 55c (as shown in FIG. 8) is a snug fit therein so that rotation of the indexing wheel 55 is prevented. In the normal or home position of the actuator 54, the head 56c of a vane 55c is located in said opening 72 in the cantilever arm 70 of the chassis 53 so that rotation of the indexing wheel 55 is prevented.

When the actuator 54 is rotated and the flange drive dog 62 engages the innermost track 67 so as to deflect the flexible portion of the flange 60 inwardly towards the indexing wheel 55, the indexing wheel drive dog 66 initially engages with a protrusion 71a extending from an inner side of the enlarged head 71 on the cantilever arm 70 of the chassis 53 so that the cantilever arm 70 is deflected outwardly, away from the indexing wheel 55, to free the head 56c of the vane 55c from the slot 72, thereby unlocking the indexing wheel 55. Only once the indexing wheel 55 has been released by the indexing wheel drive dog 66 pushing the cantilever arm 70 away from the indexing wheel 55 does the indexing wheel drive dog 66 subsequently engage a vane 55c of the indexing wheel 55 so that further rotation of the drive coupling member 57 rotates the indexing wheel 55.

Prior to the flange drive dog 62 falling off the end of the innermost track 67 and the flexible flange portion 60 returning to its undeflected state due to its resilience, the indexing wheel drive dog 66 no longer pushes against the cantilever arm 70 and so the cantilever arm 70 is free to move back towards the indexing wheel 55. As the cantilever arm 70 is free to move back just prior to rotation of the indexing wheel 55 being completed, the cantilever arm is prevented from moving all the way back by the head 56*b* of a following vane 55*b* which contacts the cantilever arm 70. During further rotation of the indexing wheel, the head 56*b* slides across the cantilever arm and then drops into the opening 72 thereby allowing the cantilever arm 70 to move all the way back and locking the indexing wheel 55 in position prior to any further rotation of the drive coupling member 57 in response to continued rotation of the actuator 54.

On the return stroke of the actuator 54, it will be appreciated that deflection of the flexible flange portion 60 in the opposite direction, i.e. in a direction away from the indexing wheel, also ensures that the indexing wheel drive dog 66 clears the chassis arm 70 and so the indexing wheel 55 is not unlocked, thereby preventing any rotation of the indexing wheel 55 during the return stroke.

The blister strip drive member or indexing wheel 15 of the invention may take a slightly different form to that described with reference to FIGS. 8 to 13*b*, although the principle still remains the same. In particular, the indexing wheel 15 may be used to squeeze the used blister cavities as they pass around it, thereby at least partially crushing them. This is achieved by enlarging the axle or hub 18 of the indexing wheel so that the distance (X in FIG. 14) between the hub and the casing or wall of the device 11, or a component fixed to the casing 11, is less than the maximum height of a blister cavity. As the blister cavities are entrained between the spokes 17*a* of the indexing wheel 17, onward rotation of the wheel 17 causes the cavities to be at least partially squashed or sandwiched between the enlarged hub 18 of the indexing wheel 17 and the casing 11 of the device. The advantage of at least partially crushing the empty blister cavities is that they then take up less space when coiled within the used blister chamber of the device as the coiled strip has a smaller diameter. Furthermore, a natural curvature is imparted to the strip, both as a result of being fed around the blister drive wheel and also as a result of the crushing of the blister cavities. This encourages the used portion of the strip to coil more readily. It is also apparent that, when the blister cavities have been crushed, the cavity is more resilient to denting at the point at which the spoke of the blister drive wheel contacts the strip, i.e. at the root where the blister cavity meets the remainder of the strip. Therefore, a more positive and precise drive of the strip is achieved when the blisters have been crushed.

As mentioned above, the drive coupling member 57 of the inhaler of the present invention is modified in that the drive gear 16 is attached thereto in place of the actuator 54 so that the drive coupling member 57 rotates in response to rotation of the drive gear 16. It is also envisaged that the drive gear 16 may be moulded integrally with the drive coupling member 57.

Figure 7:
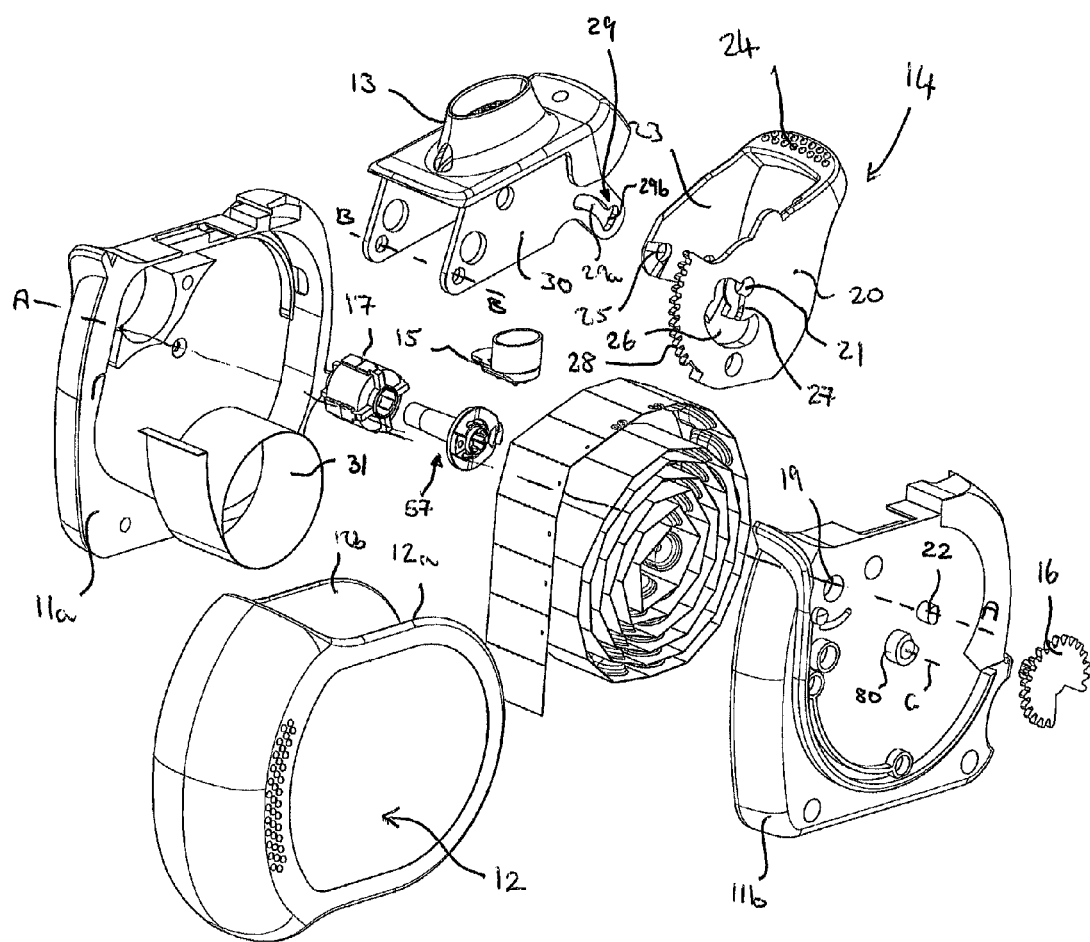
FIG. 7 is an exploded perspective view showing the individual components of the inhaler according to the invention.

It will be apparent from FIG. 7, that the drive coupling member 57 extends into an opening 19 in a side wall of the shell 11*b* of the housing 11 and the drive gear 16 is coupled thereto so that it is disposed on the outside surface of said side wall, only the drive coupling member 57, the blister strip drive wheel 17 and the blister strip itself, being received within the housing between the shell portions 11*a*, 11*b*.

Figure 15:
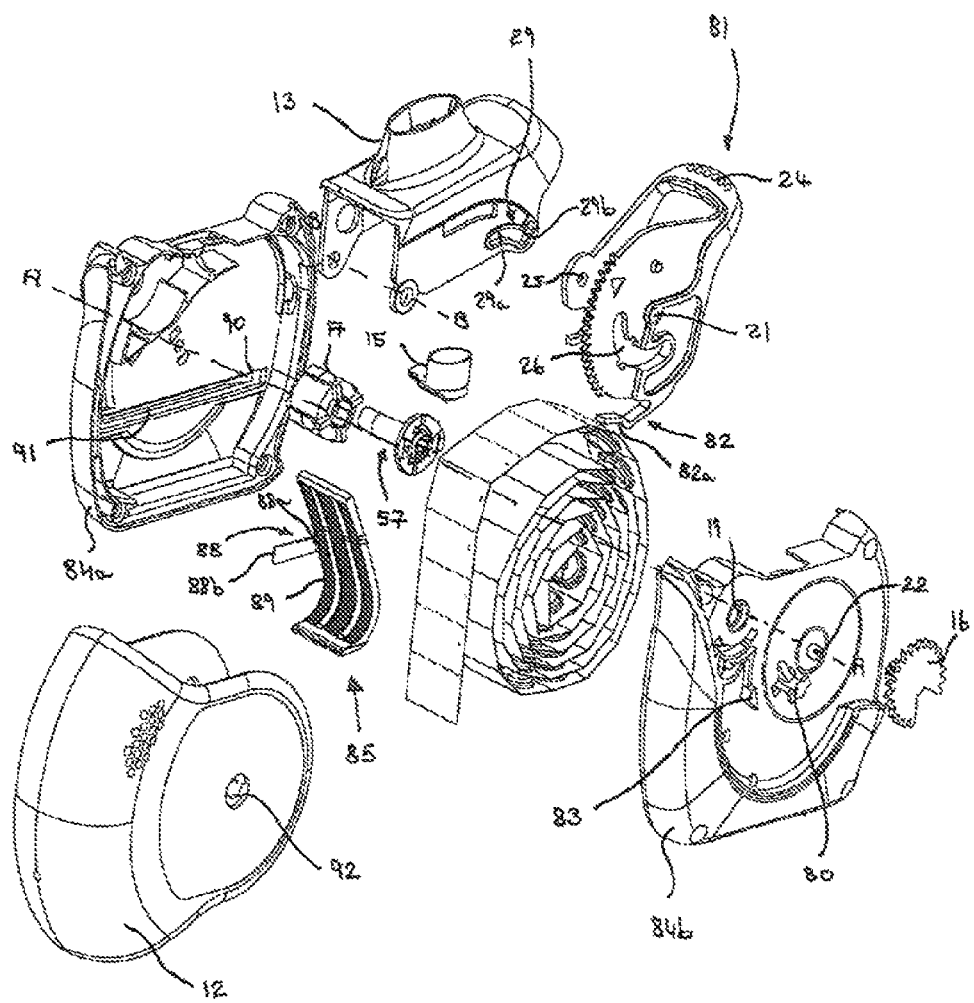
FIG. 15 is an exploded perspective view showing the individual components of the inhaler according to another embodiment of the invention.

The actuating lever 14 has a first plate-like portion 20 that extends across the outside surface of the shell lib and has a hole 21 therein to receive a boss 22 upstanding from said surface, to pivotally mount the actuating lever 14 to the shell 11 for rotation about a second axis (A-A in FIGS. 7 and 15). The actuating lever 14 may also have a second plate-like portion 23 that is parallel to and spaced from the first portion 20 by an actuating button 24. The second plate-like portion extends across the opposite surface of the shell 11*a* and also has a hole 25 to engage with a corresponding boss upstanding from said opposite surface so as to pivotally couple the actuating member 14 to the shell 11 with the actuating button extending between the plates 20,23 and opposite surfaces of the shell portions 11*a*, 11*b*.

The first plate 20 has a further aperture 26 therein and the cap 12 is pivotally mounted to the outer shell portion 11*b* by a coupling such as a boss 80 upstanding from a surface of the shell portion 11*b* that locates in a corresponding recess (not shown in FIG. 7, but see hole 92 in FIG. 15) in the cap 12, for rotation of the cap 12 about a third axis. The boss 80 extends through the aperture 26 in the actuating member 14. The aperture 26 is arcuately-shaped and has the second axis as its centre so that, when the actuating lever 14 is rotated about the second axis, the boss 80 travels within the aperture 26 without engaging the actuating member 14, and so the cap 12 remains stationary. The actuately-shaped aperture 26 acts as a clearance hole for the pivotal attachment of the cap 12 to the shell 11*b* and so as to allow rotation of the actuating lever 14 about the second axis.

A drive member (not shown) extends from an inner surface of the cap 12. The drive member is located between, and spaced from, each of the second and third axes and extends towards the actuating lever 14 and the actuating lever 14 includes a wall 27 for engagement by said drive member when the cap 12 is rotated it about its third axis back towards its closed position and after the actuating member 14 has been rotated about its second axis. The drive member and wall 27 meet at a location between the second and third axes so that, upon further rotation of the cap 12 back towards its closed position, the drive member pushes against the wall 27. Pressure of the drive member against the wall 27 causes the actuating member 14 to rotate back into its original position, together with the cap 12 into its closed position.

The cap 12 and actuating lever 14 are configured so that, when the cap 12 is in its closed position and the actuating lever 14 has returned to its initial position, the cap 12 overlies the actuating button 24 which is pressed by a user to operate the device. This prevents a user from attempting to operate the device by rotating the actuating member 14 prior to opening the cap 12.

The actuating member 14 has a gear segment 28 that drivingly meshes with the gear drive 16 so that rotation of the actuating member 14 also causes rotation of the gear drive 16 and selective rotation of the blister strip drive member relative to the gear drive 16 whilst the actuating member 14 is rotated through the initial portion of its stroke, due to the indexing mechanism described above, so that the blister strip is initially driven to move the next blister into alignment with the blister piercing member 15. During further rotation of the actuating member 14 through the second portion of its stroke, the blister strip is prevented from moving as the drive coupling member 57 is de-coupled from the blister strip drive wheel 17. During rotation through the second portion of its stroke, the blister piercing member 15 carried by the mouthpiece 13 is rotated so that it pierces the aligned, and now stationary, blister.

A cam drive member (not shown) extends from the first plate 20 towards the second plate 23. The cam drive member is received in a cam groove or slot 29 formed in a peripheral wall 30 depending from the mouthpiece 13. As is apparent from FIG. 7, the cam groove or slot 29 has an arcuate portion 29*a* followed by a leg portion 29*b* at one end. It will be appreciated that the slot 29 may alternatively be provided in the actuating lever 14 and the cam drive member may extend from the mouthpiece 13 to achieve the same function.

During initial rotation of the actuating member 14 through the first portion of its stroke, the cam drive member slides along the arcuate portion 29 of the cam slot 29 without causing any movement of the mouthpiece 13, as the arcuate portion 29a of the cam slot 29 has the second axis as its radius. However, during subsequent rotation of the actuating member 14, the cam member reaches the leg portion 29b of the cam slot 29 and engages the side walls of the cam groove 29 so as to cause the mouthpiece 13 to rotate about a first axis B-B together with the actuating member 14 thereby pulling the blister piercing member 15, depending from the mouthpiece 13, into the aligned blister.

Although reference is made to a pivoting mouthpiece 13, it will also be appreciated that, in an alternative embodiment, the blister piercing member 15 may be pivotally attached to a mouthpiece 13 or mounted in a support or module that is pivotally attached to the mouthpiece 13. In these embodiments, the mouthpiece 13 itself remains stationary so that, in response to operation of the actuating member 14, the blister piercing member 15 pivots relative to the stationary mouthpiece 13 to puncture the lid of an aligned blister.

During rotation of the cap 12 from its open to its closed position, rotation of the actuating member 14 due to rotation of the cap 12 also causes rotation of the mouthpiece back to its original position as the cam member travels back along the cam slot 29b.

As shown in FIG. 7, a spiral element 31 is also optionally mounted within the housing 11 into which the used portion of the strip is fed.

Although a region is provided within the housing 11 to receive the used portion of the strip, it will be appreciated that the invention is also applicable to other inhalation devices (not shown) in which used blisters are not retained within the housing 11 but pass out through an opening (not shown) in the wall of the housing 11 for periodic detachment by a user.

Although piercing of an aligned blister only occurs after movement of the strip has stopped, it is envisaged that the mechanism could be configured so that de-coupling of the blister strip drive wheel 17 and the drive coupling member 57 only occurs after the blister piercing element 15 has pierced, or begun to pierce, the lid of a blister so that the piercing element is drawn across and through the lid of the blister as it enters it. This creates a larger hole relative to the size of hole created when the strip is stationary prior to being puncturing by the blister piercing element. A larger hole can advantageously ensure that all the drug dose is entrained and removed from the blister.

Figure 16:
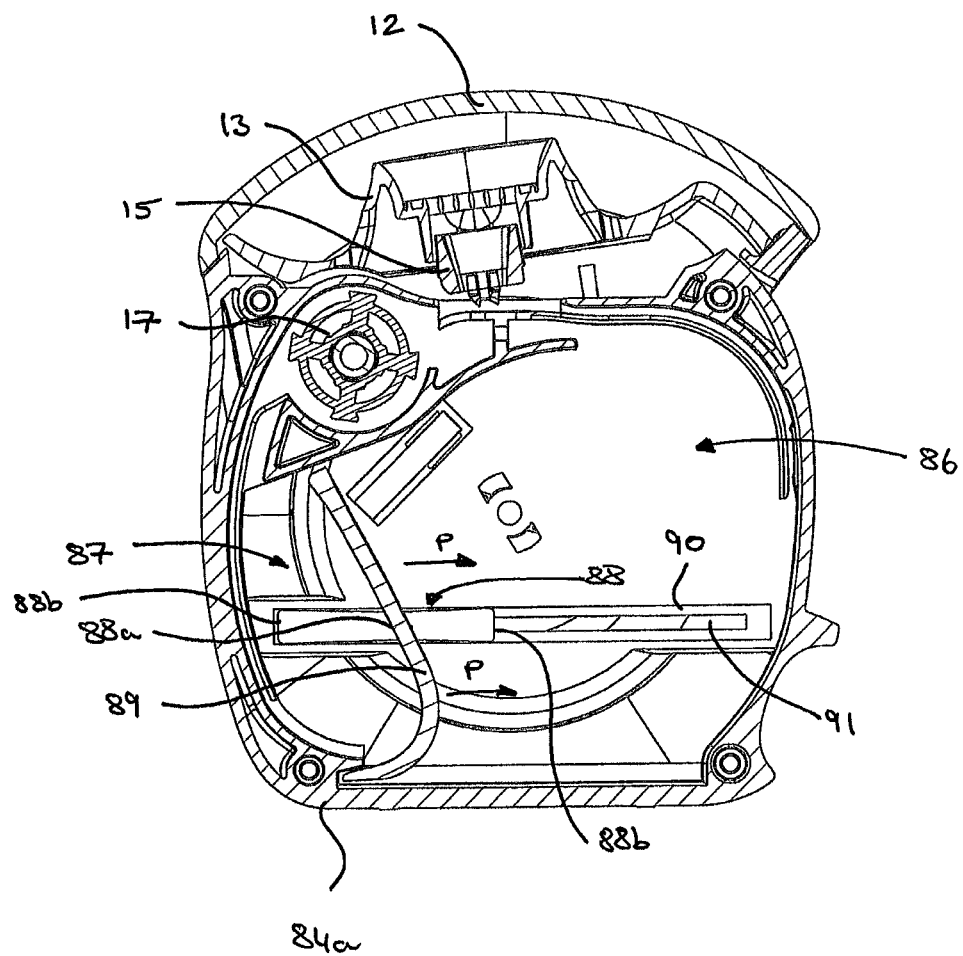
FIG. 16 is a cross-sectional side view of the inhaler shown in FIG. 15.

A modified embodiment is shown in FIGS. 15 and 16. This embodiment is similar to the previous embodiment and functions in the same way but additionally includes a detent mechanism for holding the actuating lever 81 at the end of its stroke so that a small force must be applied to it to overcome the hold placed on it by the detent mechanism and allow the actuating lever 81 to return to its initial position. The detent mechanism includes a cantilever 82 that extends from the actuating lever 81 and has a kinked region 82a which engages with a pawl 83 on the shell portion 84b as the actuating lever 81 approaches the end of the second portion of its stroke, so that the cantilever 82 is resiliently deformed and as it rides over the kinked region 82a and springs back to its original shape once the pawl 83 has cleared the kinked region 82a. When the actuating lever 81 is rotated back towards its initial position, sufficient force must initially be applied to the actuating lever 81 so that the cantilever 82 is deformed by the pawl 83 and rides back over it. In addition to providing a slight resistance to initial movement of the actuating lever 81, it also generates an audible 'click' as the end of the second portion of the stroke of the actuating lever 81 is reached and so provides an audible signal to the user that the end of the travel of the actuating lever 81 has been reached.

This embodiment also includes a rigid dividing wall 85 that separates the interior of the housing into an unused and used blister chamber 86,87 (see FIG. 16). The wall 85 is slideably mounted within the shell portion 84a of the housing so that, as more of the blisters are used, the force of the used coil of blisters in the used blister chamber 86 presses against the wall 85 and pushes it in the direction indicated by arrow 'P' in FIG. 16, to enlarge the space for the used blisters and reduce the space previously occupied by the unused blisters.

The sliding wall 85 comprises an elongate foot 88 which is attached to and integrally formed with a baffle 89 that divides the compartment. An approximate central region 88a of the foot 88 is attached to the baffle 89 so that it extends in opposite directions on either side of the baffle 89. The foot 88 is slideably received in a recess 90 formed in a wall of the housing and is wider at its ends 88b than in its centre 88a where it joins the baffle 89 so that contact with the walls of the recess 90 is primarily made with the wider ends 88b of the foot 88.

A deeper, narrower recess 91 may extend deeper into the wall within the first recess 90 to receive a strengthening rib (not shown) depending from the underside of the foot 88.

Many modifications and variations of the invention falling within the terms of the following claims will be apparent to those skilled in the art and the foregoing description should be regarded as a description of the preferred embodiments of the invention only. For example, although reference is made to a "mouthpiece", the invention is also applicable to devices in which the dose is inhaled through the nasal passages. Therefore, for the purposes of this specification, the term "mouthpiece" should also be construed so as to include within its scope a tube which is inserted into the nasal passages of a patient for inhalation therethrough.

Furthermore, although the blister piercing member 15 is described as being attached to the mouthpiece so that the mouthpiece 13 and the blister piercing member rotate together, it is also envisaged that the mouthpiece itself could remain stationary and the blister piercing element 15 could be pivotally mounted to the mouthpiece 13 so that the blister piercing member 15 rotates relative to the mouthpiece 15 to pierce the lid of an aligned blister.

In another embodiment, the cap and the actuating member could be combined into a single component so that rotation of the cap also causes indexing of the strip and piercing of an aligned blister.

It will be appreciated that the inhaler of the invention may be either a passive or active device. In a passive device, the dose is entrained in a flow of air caused when the user inhales through the mouthpiece. However, in an active device, the inhaler would include means for generating a pressurised flow of gas or air through the blister to entrain the dose and carry it out of the blister through the mouthpiece and into the user's airway. In one embodiment, the inhaler may be provided with a source of pressurised gas or air within the housing.

The invention claimed is:

1. An inhaler comprising a housing to receive a strip having a plurality of blisters, each blister having a puncturable lid and containing a dose of medicament for inhalation by a user, a mouthpiece mounted to the housing and through which a dose of medicament is inhaled by a user, a blister piercing member mounted for rotation about a first axis and an actuating mechanism including an actuating lever mounted for rotation about a second axis to sequentially move each blister into alignment with the blister piercing member, wherein the actuating lever cooperates with the blister piercing member so that the blister piercing member pivots about said first axis in response to rotation of the actuating member from an initial position about the second axis to puncture the lid of an aligned blister so an airflow through the blister is generated to entrain the dose contained therein and carry it, via the mouthpiece, into the user's airway when a user inhales through the mouthpiece;

wherein the housing comprises a shell and the actuating lever is mounted for rotation about the second axis on the shell and includes a mounting plate that extends within a space between the shell and a cap, the cap covering the mouthpiece in a closed position.

2. An inhaler according to claim 1, wherein the blister piercing member is immovably attached to the mouthpiece and the mouthpiece is pivotally mounted to the housing so that the mouthpiece pivots, together with the blister piercing member, about said first axis in response to rotation of the actuating lever about the second axis.

3. An inhaler according to claim 1, wherein the actuating mechanism is configured such that the actuating lever and blister strip drive wheel disengage at the end of the first portion of the stroke so that the blister strip drive wheel remains substantially stationary during rotation of the actuating lever through said second portion of its stroke.

4. An inhaler according to claim 3, wherein the actuating mechanism comprises a drive coupling member rotatable in response to rotation of the actuating lever to rotate the blister strip drive wheel, the blister strip drive wheel being rotatably mounted on said drive coupling member, wherein the actuating mechanism includes means to control rotation of the blister strip drive wheel relative to rotation of the drive coupling member so that the blister strip drive wheel rotates together with the drive coupling member during the first portion of the stroke of the actuating lever but not during the second portion of the stroke of the actuating lever.

5. An inhaler according to claim 4, wherein said means for controlling rotation of the blister strip drive wheel is also configured to inhibit rotation of the blister strip drive wheel when the actuating lever is rotated in the opposite direction.

6. An inhaler according to claim 4, wherein the drive coupling member includes a drive gear rotatable together with the drive coupling member and the actuating lever includes a drive gear segment that drivingly engages with the drive gear so that the drive gear rotates in response to rotation of the actuating lever to rotate the drive coupling member.

7. An inhaler according to claim 4, wherein the means to control rotation of the blister strip drive wheel includes cooperating elements on the drive coupling member and on the housing.

8. An inhaler according to claim 1, wherein the blister piercing member is immovably attached to the mouthpiece and the mouthpiece is pivotally mounted to the housing so that the mouthpiece pivots, together with the blister piercing member, about said first axis in response to rotation of the actuating lever about the second axis and wherein one of the actuating lever and the mouthpiece has a drive cam element and the other of the actuating lever and the mouthpiece has a drive cam surface, wherein the drive cam element cooperates with the drive cam surface so that the mouthpiece pivots about said first axis in response to rotation of the actuating member about the second axis to puncture the lid of an aligned blister.

9. An inhaler according to claim 8, wherein the drive cam surface includes a cam groove, the cam groove having an arcuately shaped region having an axis that corresponds to the second axis about which the actuating lever rotates such that, during said initial rotation of the actuating lever through a first portion of its stroke, the drive cam element slides along said arcuately shaped region of the cam groove without causing rotation of the mouthpiece about the first axis.

10. An inhaler according to claim 9, wherein the cam groove has a second region shaped such that, during further rotation of the actuating lever through a second portion of its stroke, cooperation between the drive cam element and the second region of the cam groove causes the mouthpiece to rotate together with the actuating lever so that the blister piercing element punctures the lid of an aligned blister.

11. An inhaler according to claim 1, comprising a coupling pivotally mounting the cap to the housing for rotation about a third axis.

12. An inhaler according to claim 1, wherein the actuating lever comprises a button extending from said plate and protruding out of said space to enable actuation of the actuating lever by a user.

13. An inhaler according to claim 1, wherein the actuating lever comprises an arcuately shaped opening extending about the second axis, the coupling that pivotally mounts the cap to the housing extending through said opening so that the coupling travels along the arcuately shaped opening as the actuating lever pivots about the second axis.

14. An inhaler according to claim 13, wherein the cap and actuating lever include cooperating means configured such that, when the cap is rotated from its open position back into its closed position in which it covers the mouthpiece, the actuating lever is rotated back into its initial position.

15. An inhaler according to claim 14, wherein the cooperating means comprises a wall on the actuating lever and a drive member depending from the cap towards the actuating lever, said wall and drive member being positioned between the second and third axes such that the drive member engages the wall when the cap is rotated in a direction back into its closed position to rotate the actuating member about the second axis back into its initial position.

16. An inhaler according to claim 1, comprising a detent mechanism including a cantilevered arm on the actuating lever and a pawl on the shell, the arm being resiliently deformed by said pawl as the actuating lever reaches the end of the second portion of its stroke, to hold the actuating lever in position until the cap is closed.

17. An inhaler according to claim 16, wherein the cantilevered arm includes a kinked portion that snaps over the pawl when the actuating lever is rotated towards the end portion of its stroke.

18. An inhaler according to claim 1, wherein the actuating lever is pivotable in the same direction about the second axis to sequentially move each blister into alignment with a blister piercing member and to cause rotation of the blister piercing member about the first axis so that the blister piercing member punctures the lid of an aligned blister.

19. An inhaler according to claim 18, wherein the actuating mechanism is configured such that rotation of the actuating lever about the second axis through a first portion of its stroke moves a blister into alignment with a blister piercing member and, further rotation of the actuating lever about the second axis in the same direction, during a second portion of its stroke, causes rotation of the blister piercing member about the first axis so that the blister piercing member punctures the lid of an aligned blister.

20. An inhaler according to claim 19, wherein the actuating mechanism includes a blister strip drive wheel, wherein the actuating lever is engaged with said blister strip drive wheel during rotation of the actuating lever to rotate said blister strip drive wheel and drive said strip.

21. An inhaler according to claim 20, wherein the blister strip drive member comprises a plurality of spokes extending from a hub, the spokes being spaced from each other such that a spoke locates between blister cavities as a blister strip passes around the blister strip drive member to engage and drive a strip as the blister strip drive member rotates, the blister strip drive member being positioned relative to a wall such that the distance between the hub and said wall is less than the height of a blister cavity such that onward rotation of the wheel causes a blister cavity to be at least partially squashed or sandwiched between the hub and said wall.

22. An inhaler comprising a housing to receive a strip having a plurality of blisters, each blister having a puncturable lid and containing a dose of medicament for inhalation by a user, a mouthpiece mounted to the housing and through which a dose of medicament is inhaled by a user, a blister piercing member mounted for rotation about a first axis and an actuating mechanism including an actuating lever mounted for rotation about a second axis to sequentially move each blister into alignment with the blister piercing member, wherein the actuating lever cooperates with the blister piercing member so that the blister piercing member pivots about said first axis in response to rotation of the actuating member from an initial position about the second axis to puncture the lid of an aligned blister so an airflow through the blister is generated to entrain the dose contained therein and carry it, via the mouthpiece, into the user's airway when a user inhales through the mouthpiece;

wherein a wall is slideably mounted in the housing to divide it into unused and used blister compartments, the wall comprising a baffle extending between opposing walls within the housing and an elongate foot extending substantially at right-angles to the baffle and being slideably received within a recess in a wall of the housing.

23. An inhaler according to claim 22, wherein the baffle is attached to a central region of the foot.

24. An inhaler according to claim 23, wherein the foot is widest at its ends remote from the baffle such that only the ends of said foot contact the walls of said recess in the housing.

* * * * *